US005951830A

United States Patent [19]
Bertocchio et al.

[11] Patent Number: 5,951,830
[45] Date of Patent: Sep. 14, 1999

[54] PROCESS FOR PURIFICATION OF HYDROCHLOROFLUOROETHANES

[75] Inventors: Rene Bertocchio, Vourles Par Vernaison; Andre Lantz, Vernaison; Daniel Roland, Lyons; Bertrand Collier, Saint Genis Laval, all of France

[73] Assignee: Elf Atochem S.A., France

[21] Appl. No.: 08/951,476

[22] Filed: Oct. 16, 1997

[30] Foreign Application Priority Data

Oct. 18, 1996 [FR] France ................... 96 12713

[51] Int. Cl.$^6$ ............ C07C 1/00; B01D 53/00; B01D 5/00; B01D 17/06
[52] U.S. Cl. ............ 204/157.15; 205/157.3; 205/157.21; 210/748; 210/915
[58] Field of Search ............ 204/157.15, 175.3, 204/157.21; 210/748, 915

[56] References Cited

U.S. PATENT DOCUMENTS

| | | | |
|---|---|---|---|
| 4,060,469 | 11/1977 | Sweeney et al. | 204/163 R |
| 4,145,368 | 3/1979 | Sweeney et al. | 260/653 |
| 4,948,479 | 8/1990 | Brooks et al. | 204/158 |
| 5,026,930 | 6/1991 | Manzer et al. | 570/168 |

FOREIGN PATENT DOCUMENTS

| | | |
|---|---|---|
| 357 328 | 3/1990 | European Pat. Off. . |
| 357328 | 3/1990 | European Pat. Off. . |
| 370 688 | 5/1990 | European Pat. Off. . |
| 407989 | 1/1991 | European Pat. Off. . |
| 462514 | 12/1991 | European Pat. Off. . |
| 493760 | 7/1992 | European Pat. Off. . |
| 526 908 A2 | 2/1993 | European Pat. Off. . |
| 526 908 A3 | 2/1993 | European Pat. Off. . |
| 547930 | 6/1993 | European Pat. Off. . |
| 583 703 | 2/1994 | European Pat. Off. . |
| 1315351 | 12/1962 | France . |
| 2-157235 | 6/1990 | Japan . |
| 4-300842 | 10/1992 | Japan . |
| WO 92/16480 | 10/1992 | WIPO . |
| WO 93/12058 | 6/1993 | WIPO . |
| WO 93/14052 | 7/1993 | WIPO . |

OTHER PUBLICATIONS

Yoshinaga et al. Purification of hydrochlorofluorocarbons and hydrofluorocarbons vol. 118, No. 19, May 10, 1993.

French Search Report Jun. 19, 1997.

*Primary Examiner*—Kathryn Gorgos
*Assistant Examiner*—Edna Wong
*Attorney, Agent, or Firm*—Bell, Boyd & Llyod

[57] ABSTRACT

To remove the olefinic impurities from a hydrochlorofluoroethane of formula: $CF_3$—CHClX (X=H, F, or Cl), it is subjected to a photochlorination stage.

13 Claims, No Drawings

PROCESS FOR PURIFICATION OF HYDROCHLOROFLUOROETHANES

FIELD OF THE INVENTION

The present invention relates to the field of hydrochlorofluoroalkanes, generally referred to under the term HCFC, and its subject-matter is more particularly the purification of hydrochlorofluoroethanes of formula $CF_3$—$CHClX$, X denoting a hydrogen, fluorine or chlorine atom.

BACKGROUND OF THE INVENTION

1-Chloro-2,2,2-trifluoroethane, 1,1-dichloro-2,2,2-trifluoroethane and 1-chloro-1,2,2,2-tetrafluoroethane, known in the trade under the designations F133a, F123 and F124 respectively, are obtained industrially by catalytic fluorination of chlorinated olefins like trichloroethylene or perchloroethylene or of fluorinated intermediates like 1,1,2-trichloro-2,2-difluoroethane (F122), it being possible for this operation to be carried out either in the gas phase or in the liquid phase.

In the liquid phase the reaction is generally catalysed with antimony halides (see, for example, European Patents 462 514 and 547 930, relating to F133a). Numerous catalysts have been proposed for gas-phase fluorination, especially Zn, Ni, Mn, Mg, Fe, Co or Cr oxides or halides, either in bulk or preferably deposited on supports such as alumina or fluorinated alumina (Patents EP 583 703, U.S. Pat. No. 5,026,930 and WO92/16480 in the case of F133a, and Patents FR 1 315 351 or JP 2157235 in the case of F123).

Although the selectivities of these fluorinations are generally good, the products obtained are nevertheless accompanied by a number of impurities, especially of more or less fluorinated compounds ($CF_2ClCH_2Cl$, $CFCl_2CH_2Cl$, $CF_3CH_2F$, $CF_3CHCl_2$, $CF_3CH_3$), of $C_2$ olefins such as $CF_2$=$CHCl$, $CF_2$=$CFCl$, $CF_2$=$CCl_2$ and $CFCl$=$CCl_2$, and of $C_4$ olefins such as $CF_3CH$=$CHCF_3$, $CF_3CH$=$CFCF_3$, $CF_3CH$=$CClCF_3$ and $CF_3CF$=$CClCF_3$.

These impurities are obtained in larger quantities in the gas-phase process and, in particular, in the case where this fluorination is carried out in the presence of oxygen, to stabilize the catalyst activity (Patent EP 583 703). Thus, in the course of a fluorination of trichloroethylene (TCE) on a bulk chromium oxide, in the following conditions:

Temperature: 350° C.

Pressure: 15 bars

Contact time: 14 seconds

HF/TCE molar ratio: 10

$O_2$/TCE molar ratio: 0.06 an F133a containing approximately 3% of $C_4$ olefinic products (essentially $CF_3CH$=$CHCF_3$) was obtained.

These $C_4$ impurities are particularly difficult to remove because they have volatilities which are very close to those of the products sought after, especially of F133a or F123, and some of them are particularly toxic.

F123 is employed in the refrigeration industry, in particular in air-conditioning plants. It is also employed as a synthesis intermediate.

F133a is employed industrially as an intermediate product for the manufacture of HALOTHANE $CF_3CHBrCl$, which is an anaesthetic agent, or for the manufacture of trifluoroethanol $CF_3CH_2OH$ which itself is used essentially for the manufacture of other anaesthetic agents like ISOFLURANE ($CF_3CHClOCHF_2$) and DESFLURANE ($CF_3CHFOCHF_2$). The purity standards required for these products are such that it is advantageous to employ an F133a which is as pure as possible and which in particular contains no products capable of yielding toxic impurities.

Another essential application of F133a is at the present time the industrial manufacture of 1,1,1,2-tetrafluoroethane (F134a), one of the hydrofluoroalkanes which have replaced the chlorofluoroalkanes because of the impact of the latter on the stratospheric ozone layer.

The fluorination of F133a to F134a is generally carried out in the gas phase at temperatures of the order of 350–400° C., in the presence of an excess of HF.

A number of olefinic impurities formed during this fluorination of F133a to F134a are the same ones as those liable to be formed during the manufacture of F133a and to preexist in the F133a employed as raw material for this second fluorination.

The purification of F123 and, in particular, the removal of its olefinic impurities have been carried out with the aid of oxidizing agents such as alkali metal permanganates (Patent EP 357 328) or by passing over metal oxides at temperatures which are preferably between 90 and 130° C. (Patent EP 370 688) or else by treatment with the aid of hydrides and/or strong bases (Patent EP 493 760).

Like other hydrochlorofluorocarbons, F123 and F124 can also be rid of their olefinic impurities by catalytic hydrogenation as indicated in Patent Application WO 93/14052.

To our knowledge, no document exists describing a process for specific purification of F133a and, in particular, a removal of olefins present in F133a.

DESCRIPTION OF THE INVENTION

The present invention is therefore aimed at a process for purification of hydrochlorofluoroethanes, in particular of F133a, in order to remove the olefinic products therefrom, and especially the $C_4$ olefins like $C_4F_7H$, $C_4F_6H_2$, $C_4F_6HCl$ and $C_4F_6Cl_2$, some of which are very difficult to separate by distillation from the product to be purified.

It is known, furthermore, that F133a can be easily chlorinated to give F123 and F113a ($CF_3CCl_3$). Such chlorinations can be carried out using thermal initiation in the presence or in the absence of catalysts (Patents EP 526 908 and U.S. Pat. No. 4,145,368) and using photochemical initiation (Patents U.S. Pat. No. 4,060,469 and EP 407 989). These photochemical chlorinations, which can be carried out equally well in the gas phase (U.S. Pat. No. 4 060 469) and in the liquid phase (Patent EP 407 989) are so easy that they form the basis of various processes for the manufacture of F123.

It has now been found that, despite the high reactivity of F133a and of hydrochlorofluoroethanes with regard to photochlorination, the use of a moderate quantity of chlorine allows the chlorination of the olefinic impurities to be carried out very selectively, that is to say without chlorinating in an unacceptable manner the F133a or the product to be purified. By photochlorination, it is thus possible to remove the olefinic impurities (in particular the $C_4$ olefinic impurities) from a hydrochlorofluoroethane of formula $CF_3$—$CHClX$, X denoting a hydrogen, fluorine or chlorine atom.

The subject-matter of the invention is therefore a process for purification of such a hydrochlorofluoroethane containing olefinic impurities, characterized in that it includes a stage consisting in subjecting the said hydrochlorofluoroethane to irradiation with ultraviolet or visible rays of wavelength of between 320 and 500 nm, in the presence of chlorine.

In order to be able to remove entirely all the undesirable olefinic impurities a molar ratio: chlorine/olefinic impurities of between 0.75 and 20, preferably between 0.9 and 1.5, is employed. The optimum value of this ratio depends on the initial concentration of olefins and on the desired degree of purification.

The photochemical chlorination according to the invention can be carried out in the gas phase or in the liquid phase. "Liquid phase" is here intended to mean either a liquid under autogenous pressure or a solution in a solvent which is transparent to the radiation employed and inert to chlorination, like, for example, carbon tetrachloride or trifluorotrichloroethane.

On account of the boiling points of F133a (6.1° C.), of F123 (27° C.) and of F124a (−12° C.), the photochlorination can be carried out in the liquid phase at atmospheric pressure by cooling the crude hydrochlorofluoroethane to be purified, sufficiently to keep it in the liquid state. It is preferable, however, to operate at a slight pressure, so as to be able to perform the chlorination at ambient temperature without excessive cooling and to avoid any loss of products by volatilization. In these conditions of chlorination in the liquid phase the temperature may vary within a very wide range, for example from −35° C. to the boiling temperature of the product to be purified at the pressure employed, but it is generally preferred to work at a temperature of between 10 and 50° C., so as to minimize the energy expenditure needed for cooling or heating and to be able to keep the product at a relatively slightly raised pressure (lower than 5 bars).

The chlorination can also be carried out in the gas phase at a temperature of the order of −12 to 100° C. but, in this case too, the temperature is preferably kept between 10 and 50° C. In these conditions the reaction is preferably conducted at atmospheric pressure or at a pressure which is very slightly above atmospheric pressure.

The light energy required to catalyse the chlorination reaction is generally inversely proportional to the residence time of the material in the photochlorination reactor. It can lie between 5 and 1000 kJ/h/l and, preferably, between 50 and 500 kJ/h/l, depending on the respective concentrations of olefins and chlorine.

The crude hydrochlorofluoroethane to be purified by the photochlorination process according to the invention may contain variable quantities of olefinic compounds. The quantities and the nature of these compounds depend essentially on the conditions in which the hydrochlorofluoroethane was obtained and on the various treatments (for example distillation) carried out on the crude product before the photochlorination stage. The main $C_4$ impurities which may be present in the F133a or the F123 and which can be removed by the process according to the invention are—without any limitation being implied—fluorinated butenes such as $CF_3CH=CHCF_3$, $CF_3CCl=CHCF_3$ and $CF_3CF=CHCF_3$. The process also makes it possible to remove other olefins, such as $CF_2=CFCl$, $CF_2=CCl_2$, $CCl_2=CFCl$, F1122 ($CHCl=CF_2$) and partially fluorinated propenes ($CF_3CH=CH_2$, $CF_3CF=CH_2$, $CF_3CH=CHF$, $CF_3CF=CHF$ and $CF_3CH=CF_2$). As mentioned above, the removal of $C_4$ olefins is particularly important for, because of their physical and chemical properties, $C_4$ olefins are difficult to separate from F133a or from F123 by other purification techniques. In the case of F124a the impurities tend to be $C_2$ or $C_3$ olefins like F1122 and the abovementioned partially fluorinated propenes.

The materials to be purified may contain from about ten ppm to several parts per hundred of $C_4$ olefinic compounds. The purification process which is the subject-matter of the present invention makes it possible to completely remove these olefins, as well as other olefins that may be present in the hydrochlorofluoroethane, even in very low concentrations.

The chlorination of the olefins yields chlorine compounds which have boiling points that are much higher than those of the starting materials. Thus:

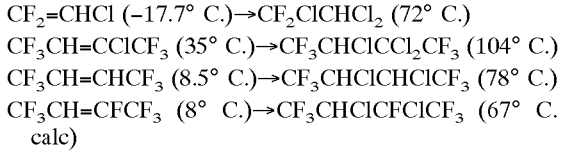

$CF_2=CHCl$ (−17.7° C.)→$CF_2ClCHCl_2$ (72° C.)
$CF_3CH=CClCF_3$ (35° C.)→$CF_3CHClCCl_2CF_3$ (104° C.)
$CF_3CH=CHCF_3$ (8.5° C.)→$CF_3CHClCHClCF_3$ (78° C.)
$CF_3CH=CFCF_3$ (8° C.)→$CF_3CHClCFClCF_3$ (67° C. calc)

Consequently, these chlorine compounds can subsequently be separated from the treated F133a, F123 or F124a merely by distillation. Since the possible products of chlorination are also less volatile than the material to be treated, a purification by photochlorination followed by a distillation enables an F133a, F123 of F124a of excellent purity to be obtained.

EXAMPLES

The following examples illustrate the invention without limiting it. Unless stated otherwise, the parts per million (ppm) are by weight.

Example 1

A photochemical reactor was employed consisting of a Pyrex glass coil of a total length of 0.945 m made of 12/14 mm tubing wound over a height of 110 mm around an emitter of UV/visible light.

The whole was placed inside a cylindrical jar with a reflecting wall 250 mm in diameter. The coil, with a total volume of 106 ml, comprised 5.5 turns of 47 mm internal diameter; downstream it was coupled to a condenser maintained at the temperature of 10° C., followed by a sampling point. Upstream there was a mixing chamber, a chlorine gas entry and a peristaltic pump continuously delivering the solution to be treated; the chlorine flow rate was adjusted with the aid of a mass flowmeter to the flow rate of the solution and to its olefin concentration.

The light source consisted of a Heraeus TQ 150 high-pressure mercury vapour lamp delivering a radiant power of 16 watts in the 320–500 nm band. The lamp was cooled by a concentric quartz jacket of 38 mm external diameter; the length of the luminous arc was 41 mm.

The coil was fed with a solution in trifluorotrichloroethane (F113) containing 25% by weight of a crude F133a containing, by weight:

| | | |
|---|---|---|
| 90.0% | of | F133a |
| 9.35% | of | trans $C_4F_7H$ + $C_4F_6H_2$ with 80% of trans $C_4F_7H$ |
| 0.2% | of | cis $C_4F_7H$ |
| 0.45% | of | $C_4F_6HCl$ | in which gaseous chlorine was bubbled and dissolved at a flow rate of 3.42 l/h (0.15 mol/h). The flow rate of the solution was 530 ml/h and, in these conditions, the molar ratio $Cl_2$/olefins ($C_4F_7H$, $C_4F_6H_2$ and $C_4F_6HCl$) was equal to 1, with a chlorine concentration of 0.28 mole/liter). The flow rates of reactants corresponded to an exposure time of 720 seconds.

After switching on the lamp and bringing the whole to running conditions, two 3-ml samples of solution were taken at the entry and exit of the photochlorinator and were analysed by vapour phase chromatography. After normalizing the areas of the two chromatograms it was found that 98.7% of the trans $C_4F_7H+C_4F_6H_2$ group and 99% of the cis $C_4F_7H$ had been removed, while only 2.1% of the F133a present was lost.

The solution obtained at the exit of the reactor contained, by weight:

21.78% of F133a
0.03% of trans $C_4F_7H+C_4F_6H_2$
0.63% of F123
<0.01% of $C_4F_6HCl$
2.6% of $C_4F_7HCl_2$ (products of chlorination of $C_4F_7H$, 2 isomers)
0.6% of $C_4F_6H_2Cl_2$ (products of chlorination of $C_4F_6H_2$)
0.15% of $C_4F_6HCl_3$ (product of chlorination of $C_4F_6HCl$).

After distillation to remove the solvent (F113) and the chlorination products, an F133a purified to 99.86% of F133a, now containing only 1400 ppm of olefins, was obtained.

Example 2

In a thick-walled Pyrex tube of 12/18 mm diameter was placed a mixture of 6.51 g of pure F133a and 0.487 g of olefins $C_4F_7H/C_4F_6H_2$ (11.2 mol % of trans $C_4F_7H$), to which 0.24 g of chlorine (3.3 mmol) was added.

The tube was sealed and exposed for 45 minutes to the light emitted by a tubular UV lamp 210 mm in length and 15.5 mm in diameter and with an electrical power of 6 watts, emitting a radiation centered on the 365 nm wavelength. The axis of the tube was placed in parallel to that of the lamp and 40 mm from the latter.

After the test the tube was opened and its content, recovered in a sufficient volume of $CCl_4$, was analysed by gas phase chromatography. It was found that 99.3% of the olefins were removed in the form of $C_4F_6H_2Cl_2$ and $C_4F_7HCl_2$, whereas only 0.60% of the F133a was converted to F123 (0.54%) and to 1,1,1 trifluoro 2,2,2 trichloroethane (F113a) (0.06%)

Example 3

The same device as in Example 2 was employed, the F133a being replaced with a sample of F124 still containing 300 ppm of F1122 ($CF_2=CHCl$).

7 g of this sample were placed in a 12-mm internal diameter thick-walled Pyrex tube and 0.5 ml of chlorine gas, measured in standard temperature and pressure conditions, was added using a suitable device.

The tube was then sealed and exposed for 80 minutes to the radiation of the lamp employed in Example 2. After opening the tube at the end of the test and recovering its content in a sufficient volume of trifluorotrichloroethane (F113), chromatographic analysis showed that the concentration of F1122 in the purified F124 had fallen to 4 ppm and that only 1.2% of the F124 had been chlorinated to F122 ($CF_2ClCHCl_2$), easily separable by distillation (b.p. 71° C.).

Example 4

A crude F133a containing 1.5% by weight of olefins trans $C_4F_7H$ and $C_4F_6H_2$ was sampled in the gas phase and mixed with a chlorine gas stream and then introduced into a Pyrex glass coil with a total capacity of 255 ml, consisting of 10 turns of 110 mm diameter made of 10/12 mm tubing and on the axis of which was placed the lamp employed in Example 1.

The gas flow rate of F133a (2 l/h) was regulated with the aid of a mass flowmeter and the volume of chlorine needed to obtain a $Cl_2$/olefins molar ratio equal to 10 was introduced with the aid of an apparatus of the syringe drive type, diluted to 25% in nitrogen.

Vapour phase chromatography analysis of the F133a thus treated showed that the relative concentration of olefins $C_4F_7H$ and $C_4F_6H_2$ had changed from 1.5% to 1035 ppm.

Example 5

Through an annular reactor with a capacity of 100 ml was circulated an impure F133a containing 4% by weight of the two olefins $C_4F_7H$ and $C_4F_6H_2$ and 0.5% of $C_4F_6HCl$. At its center the apparatus contained a lamp carrier in which a Hanau TQ 150 Z1 photoemitter tube had been placed, the main emission lines of which are at 366, 405, 417 and 436 nm.

The reactor itself consisted of an annular space bounded by two Pyrex tubes 1.8 mm in thickness and 38 and 46.6 mm in diameter respectively; the maximum path of the radiation through the reaction mixture therefore did not exceed 8.6 mm. The working height was 18 cm and the apparatus was designed to withstand a working pressure of 4.5 bars.

The F133a was injected at a flow rate of 550 ml/h with the aid of a metering pump and mixed with a chlorine gas flow rate of 0.31 mol/h. At the exit of the photochlorinator the mixture was cooled to 0° C. and analysed by gas phase chromatography. It contained, by weight, 90.91% of F133a, 0.02% of $C_4F_7H/C_4F_6H_2$, 0.006% of $C_4F_6HCl$, 2.9% of F123 and 6.1% of products of chlorination of the olefins $C_4F_6H_2Cl_2$, $C_4F_7HCl_2$ and $C_4F_6HCl_3$.

After distillation and removal of the heavy fractions, an F133a with a purity of 99.97% by weight as finally obtained, containing less than 10 ppm of $C_4F_6HCl$ and 215 ppm of olefins $C_4F_7H$ and $C_4F_6H_2$. The loss of F133a during the purification operation amounted to 2.45%.

Example 6 ough a Pyrex glass reactor consisting of a coil with adjoining turns made of 8/10 mm tubing and with a capacity of 40 ml was circulated a solution containing 2 mol % of F123 in carbon tetrachloride; the F123 employed contained 400 ppm of olefin $C_4F_6HCl$ ($CF_3CCl=CHCF_3$). The same lamp as in Example 1 was placed on the axis of the coil, but 75% of its area was obscured by a black screen.

Chromatographic analysis of the exit flow showed that only 2.5% of the F123 was chlorinated to F113a, whereas 94.9% of the olefin was removed in the form of $C_4F_6HCl_3$, a product which can be easily separated from F123 by distillation. After removal of $CCl_4$ an F123 now containing only 26 ppm of olefins $C_4F_6HCl$ was thus obtained.

Example 7

A vertical annular circulation reactor with a total volume of 350 ml was employed, the outer wall of which had an internal diameter of 50.4 mm and the inner wall consisted of a Pyrex lamp-carrier tube of 20 mm external diameter, and a jacket 70.5 mm in external diameter making it possible to cool the whole reactor.

The same UV lamp as in Example 2 was placed in the tube-carrier, bounding a working volume of 285 ml between its two electrodes.

With the UV lamp switched on, the reactor was fed continuously with a 0.57 l/h stream of chlorine and a solution, in carbon tetrachloride, of a mixture of F133a and of olefins $C_4F_7H/C_4F_6H_2$ (11.2 mol % of $C_4F_7H$) containing, after dilution, 84 g/l of F133a and 5.6 g/l of the two olefins. The flow rate of solution was adjusted to 0.75 l/h so as to have a chlorine/olefins molar ratio of 0.94.

After equilibration of the chlorine concentration the chromatographic analysis of the solution at the exit of the reactor showed that 83.7% of the two olefins had been removed, the loss of F133a being only 0.33%.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the purification of a hydrochlorofluoroethane of formula $CF_3$—CHClX containing olefinic impurities wherein, X is a hydrogen, fluorine or chlorine atom, comprising the step of purifying said hydrochlorofluoroethane containing said olefinic impurities by irradiation with ultraviolet or visible rays of wavelength between 320 and 500 nm, in contact with chlorine wherein a molar ratio of chlorine to the olefinic impurities is between 0.75 and 20.

2. Process according to claim 1, wherein the irradiation is performed in the gas phase at a temperature ranging from −12 to 100°C.

3. Process according to claim 2, wherein the temperature range is between 10 and 50° C.

4. Process according to claim 1, wherein the irradiation is performed in the liquid phase at a temperature ranging from −35° C. to the boiling temperature of the hydrochlorofluoroethane at pressure employed.

5. Process according to claim 4, wherein the hydrochlorofluoroethane is in solution in a solvent which is transparent to the radiation employed and inert to chlorination.

6. Process according to claim 5, wherein the solvent is carbon tetrachloride or trichlorotrifluoroethane.

7. Process according to claim 4, wherein the temperature is between 10 and 50° C.

8. Process according to claim 1 wherein light energy is between 5 and 1000 kJ/h/l.

9. Process according to claim 8, wherein the light energy is between 50 and 500 kJ/h/l.

10. Process according to claim 1 wherein after said irradiation, the hydrochlorofluoroethane is distilled to separate off chlorine compounds.

11. Method for the purification of a hydrochlorofluoroethane before its use as synthesis intermediate comprising processing said hydrochlorofluoroethane according to claim 1.

12. Method for the purification of 1-chloro-2,2,2-trifluoroethane comprising processing said 1-chloro-2,2,2-trifluoroethane according to claim 1.

13. Process according to claim 1 wherein the molar ratio is between 0.9 and 1.5

* * * * *